(12) United States Patent
Korin

(10) Patent No.: US 6,589,323 B1
(45) Date of Patent: Jul. 8, 2003

(54) SYSTEM FOR CLEANING AIR AND METHOD FOR USING SAME

(76) Inventor: Amos Korin, 16 Mountainview, Weston, CT (US) 06883

(*) Notice: Subject to any disclaimer, the term of this patent is extended or adjusted under 35 U.S.C. 154(b) by 17 days.

(21) Appl. No.: 09/698,533

(22) Filed: Oct. 27, 2000

Related U.S. Application Data

(60) Provisional application No. 60/166,566, filed on Nov. 19, 1999.

(51) Int. Cl.[7] ............................. A61L 2/10; A62B 7/08
(52) U.S. Cl. ......................... 96/223; 96/224; 55/337; 55/459.1; 422/24; 422/121
(58) Field of Search ...................... 96/223, 224; 55/336, 55/337, 459.1, 429, DIG. 9; 422/121, 186, 186.3, 24

(56) References Cited

U.S. PATENT DOCUMENTS

| | | | |
|---|---|---|---|
| 3,870,486 A | * 3/1975 | Eriksson et al. | ......... 55/DIG. 3 |
| 3,877,902 A | * 4/1975 | Eriksson et al. | ......... 55/DIG. 3 |
| 4,162,905 A | 7/1979 | Schuler | |
| 4,217,118 A | 8/1980 | Köpf et al. | |
| 4,477,269 A | 10/1984 | Laughlin et al. | |
| 4,941,900 A | 7/1990 | Cordes | |
| 5,080,697 A | * 1/1992 | Finke | ............... 55/337 |
| 5,185,015 A | 2/1993 | Searle | |
| 5,240,478 A | * 8/1993 | Messina | ............ 95/273 |
| 5,254,147 A | * 10/1993 | Finke | ............... 55/337 |
| 5,308,368 A | * 5/1994 | Duijn | ............. 55/459.1 |
| 5,523,057 A | 6/1996 | Mazzilli | |
| 5,601,786 A | * 2/1997 | Monagan | ............. 96/224 |
| 5,616,172 A | 4/1997 | Tuckerman et al. | |
| 5,656,242 A | 8/1997 | Morrow et al. | |
| 5,743,925 A | 4/1998 | Bench | |
| 5,891,399 A | 4/1999 | Oweson | |
| 5,997,619 A | 12/1999 | Knuth et al. | |
| 6,063,170 A | * 5/2000 | Deibert | ............. 96/224 |
| 6,221,314 B1 | * 4/2001 | Bigelow | ............ 96/224 |

OTHER PUBLICATIONS

Abstract of Publication No. JP401181869A, published on Jul. 19, 1989.
Abstract of Publication No. WO99/65533A.

* cited by examiner

*Primary Examiner*—Duane Smith
*Assistant Examiner*—Minh-Chau T. Pham
(74) *Attorney, Agent, or Firm*—Ohlandt, Greeley, Ruggiero & Perle, LLP

(57) ABSTRACT

There is provided a system for cleaning a contaminated airflow. The system includes a macro-contaminant separator that creates substantially macro-contaminant free airflow, a micro-contaminant separator that creates a substantially contaminant free airflow from said substantially macro-contaminant free airflow, and a germ controlling device that kills or controlling any germs remaining in the substantially contaminant free airflow. The macro-contaminant separator may be a cyclone-type contaminant separator. The micro-contaminant separator may include a micro-particle filter, an odor adsorber, or both. The germ controlling means may be an ultraviolet light source.

23 Claims, 3 Drawing Sheets

SYSTEM FOR CLEANING AIR AND METHOD FOR USING SAME

This application claims priority under 35 U.S.C. 119(e) of U.S. Provisional Patent Application No. 60/166,566 filed on Nov. 19, 1999.

FIELD OF THE INVENTION

This invention relates to systems for decontaminating air. In particular, the present invention relates to integrated air purification systems that combine multiple levels of contaminant filtration.

BACKGROUND OF THE INVENTION

Indoor air contaminants cause major health problems, such as lung disease and allergies. The modern lifestyle and the need for energy saving dictates that closed spaces have an ever-increasing content of pollutants. The contaminants that are present in normal room air have a wide distribution of sizes. Contaminated air may include macro-particles, such as dirt, dust particles, pollens, and smoke. Micro-particles, such as bacteria, viruses, harmful chemicals, and various odoriferous molecules, are also commonly present in contaminated air.

It is frequently desirable to remove contaminants from the air in a particular environment. Air purification systems have been widely used to remove various particles from the air, such as pollen and smoke in work places, and hazardous microbial airborne particles that include the tuberculosis bacilli and other infectious respiratory organisms at hospitals. It is known to use various types of mechanical and adsorbent filter elements in portable fan-driven air purification devices for removing contaminants from the air.

Several different types of filtering stages are available for use in present-day air purification devices. Particulate air filters have many known advantages, but they do not treat microbes and vapors. In addition, with use, particulate air filters tend to become overloaded with the retained particles, which results in reduced flow and inefficient operation. Other problems include microorganism growth over the filter media. Microorganism growth over the filter media causes an air purifier to be a source of contamination rather than a contamination control unit. Similarly to particulate air filters, carbon filters have numerous advantages, especially for removing obnoxious or harmful vapors. Yet carbon filters also suffer from the same or similar problems as particulate air filters.

It is also known to use chemicals, mechanical energy, electromagnetic radiation, and electricity as germicides. A germicide is an agent that destroys a germ, which is a general designation for any microorganism, e.g., viruses, bacteria, pollen, and molds. Chemical germicides include chloride, iodine, and oxygen. Mechanical energy based germicides include ultrasound, heat, and cold. Electromagnetic radiation germicides include laser light, gamma particles, and visible-spectrum light, as well as ultraviolet light. Electricity based germicides include: high voltage, corona discharge, electrons, beta particles and ion particles.

Ultraviolet light is an effective germicide. Some inventors have used ultraviolet light in various configurations to irradiate the filter media in an attempt to kill or control microorganisms. However, direct ultraviolet radiation of unknown contaminants, especially those that may contain halogens, may form cancer causing agents such as trihalomethanes (THM). In addition, continuous direct irradiation of filter media such as HEPA filters causes photodecomposition of the filter media.

Another disadvantage to the use of ultraviolet light is that measures must be taken to remove non-biological contaminants from the air before they reach the ultraviolet light source and impair its efficiency. Otherwise, contaminants from the incoming air will settle on the surface of the ultraviolet light source and electrical contacts, resulting in the reduction of ultraviolet emission and a fire risk due to possible short circuits. Additionally, biological material must be exposed to the ultraviolet light for a sufficient period of time to achieve sterilization. Otherwise, bacteria growth on a downstream filter or chemical adsorption agent will be carried over with the released air stream.

It is possible to use an electrostatic filter upstream from the ultraviolet lamp to extract dust from the air, but such filters are often very expensive to maintain and run. Another alternative is to use a particulate air filter upstream from the ultraviolet lamp, but such a filter would have a relatively short useful life because of the large volume of air passing through the filter. Furthermore, the germicide may degrade a porous filter, thus requiring frequent replacement of it.

In general, if a greater efficiency of filtering is desired, additional stages or filtering layers are added. This, however, multiplies the cost of the initial filtering stage and frequently results in a significant pressure drop across the filter, thus requiring a higher fan capacity with greater noise and electrical consumption for maintaining a desired flow.

U.S. Pat. No. 5,891,399 issued on Apr. 6, 1999 to Owesen for Cleaning Arrangement Including Filters and Ultraviolet Radiation. This patent provides for a device having an ultraviolet light source between a particulate pre-filter and a particulate post-filter. The particulate post-filter is irradiated by the ultraviolet light source. Thus, this filter suffers from several of the problems discussed above. Specifically, the pre-filter will have a shortened useful life because of the large volume of air and particles it will be exposed to, and the post filter will have a shortened useful life because it will decompose due to the radiation from the ultraviolet light source. Furthermore, the problem of microorganism growth on the downstream side of the post-filter is not addressed. Other examples of this situation are U.S. Pat. No. 5,656,242 to Morrow et al., U.S. Pat. No. 5,616,172 to Tuckerman et al., and U.S. Pat. No. 5,523,057 to Mazzilli.

U.S. Pat. No. 5,240,478 issued on Aug. 31, 1993 to Messina for Self-Contained, Portable Room Air Treatment Apparatus and Method Therefore. This patent discloses that, as an option, a low efficiency pre-filter may be positioned overlying the HEPA filter within the open end of the outer housing underlying the air inlet cap. However, as discussed above, this is inefficient because simply stacking filters one on top of the other reduces the amount of air the filter can pull in. This is also the case for U.S. Pat. No. 5,185,015 to Searle.

U.S. Pat. No. 4,217,118 issued on Aug. 12, 1980 to Köpf et al. for Air Intake Filter with Cyclone Separator Stage and Dust Collection Pan. This patent provides a centrifuging means for causing the incoming raw air to be subjected to a dust-centrifuging, helically-swirling flow prior to enter the filter element. However, this patent envisions the claimed device as part of an internal combustion engine. Thus, the unique problems of closed spaces are not addressed. Specifically, there is no means to remove odors or microorganisms from the airflow. This is also the case with U.S. Pat. No. 4,162,905 to Schuler.

The prior art illustrates that, although many different types of air purifier presently exist, they are not completely effective in removing contaminants from the air. For example, present air purifiers do not provide effective pre-filtering of large particles. Additionally, present air purifiers do not provide efficient measures for combating biological materials. Furthermore, existing air purifiers do not provide for long-lasting and compact filtering devices. Finally, existing air purifiers do not maximize airflow while minimizing operating costs.

Accordingly, the present invention provides an improved system for cleaning air that overcomes the deficiencies set forth above with regard to conventional filtration devices. This improved system contains effective pre-filtering of macro-contaminants, efficient measures for controlling germs, and increases the period of usefulness of the micro-contaminant filter, while maximizing airflow, and minimizing bulk and operating cost.

SUMMARY OF THE INVENTION

There is provided a system for cleaning air. The system preferably comprises a macro-contaminant separator, a micro-contaminant separator, and one or more germ controlling devices.

The macro-contaminant separator causes the airflow to move in a substantially spiral motion, whereby larger contaminants are removed from the airflow by centrifugal force. The substantially spiral airflow is created by tangential entry of the airflow into the particulate separator. The macro-particle separator creates a macro-contaminant free airflow.

The micro-contaminant separator includes one or more micro-particle filters that entrap micro-particles remaining in the macro-contaminant free airflow. The micro-particle filter is preferably selected from the group comprising: glass fibers with resin, paper, and microporous membranes. The micro-contaminant separator may also include one or more odor adsorbers. The odor adsorbers contain an odor adsorbing material selected from the group consisting of: activated carbon and zeolite. Preferably, the micro-particle filters precede the odor adsorbers and the odor adsorbers are in contact with the micro-particle filters. The micro-contaminant separator creates a substantially contaminant free airflow.

The germ controlling device substantially kills or controls microorganisms, such as viruses, bacteria, pollen, and mold, remaining in the substantially contaminant free airflow. The germ controlling device may be chemical, mechanical, electromagnetic radiation, or electrical.

The airflow is moved into and within the system by a fan that produces a vacuum.

Preferably, the macro-contaminant separator is upstream of the micro-contaminant separator, while the micro-contaminant separator is upstream of the ultraviolet light source. In this arrangement, it is necessary to shield the micro-particle filters in the micro-contaminant separator from the ultraviolet light source by a partition in order to protect the micro-particle filter from photodecomposition. In addition, it is necessary to position the fan between the macro-contaminant separator and the micro-contaminant separator so that sufficient airflow is maintained between the macro-contaminant separator, the micro-contaminant separator, and the germ controlling device.

The process for using the system for cleaning an airflow comprises separating substantially all of the contaminants from the air, first, by means of centrifugal force created within the macro-contaminant separator and, second, by means of mechanical filtration by the micro-contaminant separator, then exposing the substantially contaminant free airflow to a germ controlling device, such as ultraviolet light, which is capable of controlling or killing microorganisms.

DETAILED DESCRIPTION OF THE INVENTION

Figure 1:
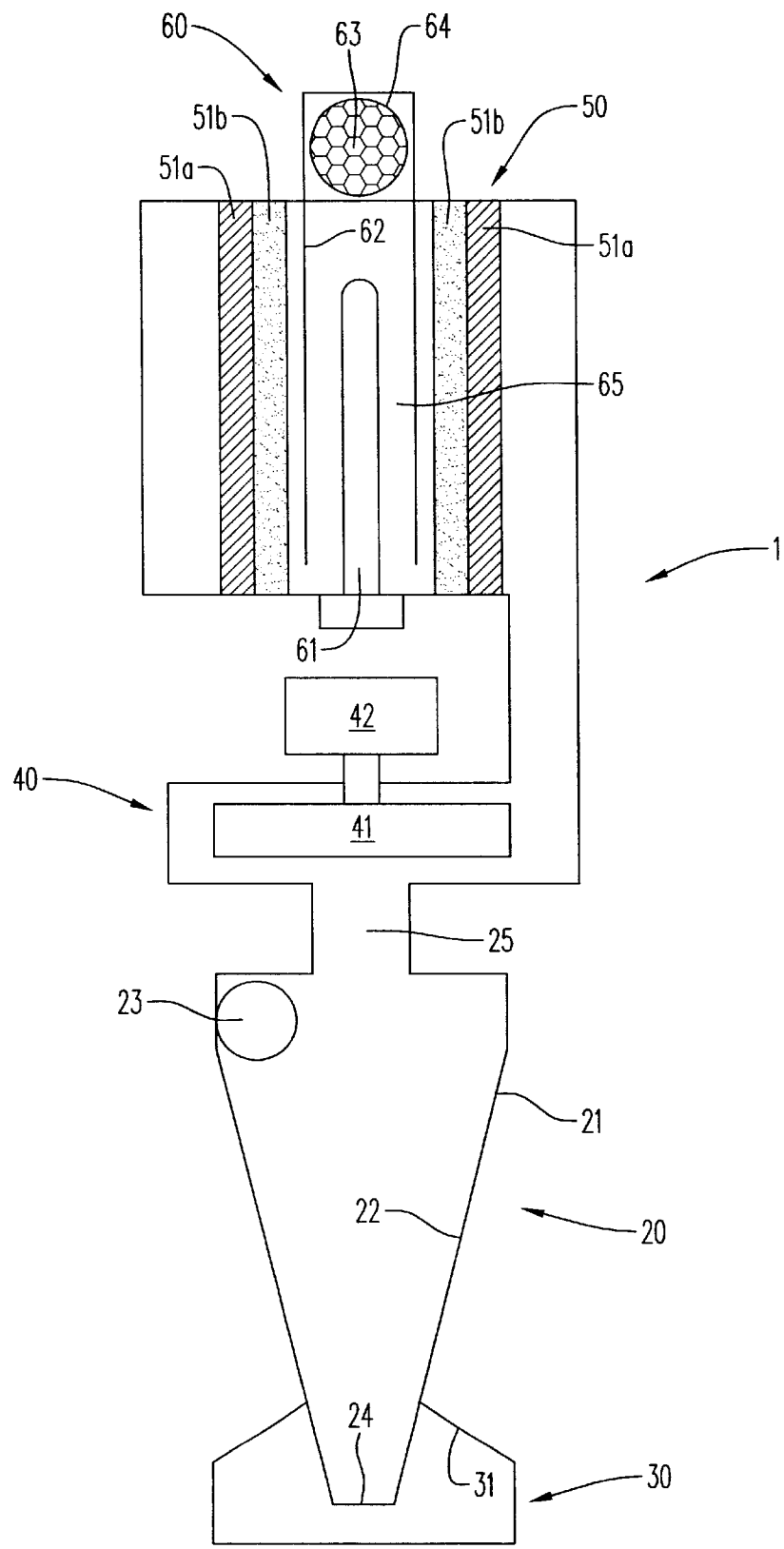
FIG. 1 is a diagram of a first embodiment of a system of cleaning air according to the present invention.

Referring to FIG. 1 shows a system for cleaning air according to the present invention, generally referred to as 1.

There is provided a frustoconical-shaped, cyclone-type, macro-contaminant separator 20 having an outer surface 21 and an interior surface 22. An air inlet 23 is provided in macro-contaminant separator 20. Air inlet 23 communicates with macro-contaminant separator 20 so as to introduce the airflow tangentially to interior surface 22.

A macro-contaminant outlet 24 is located at the bottom of macro-contaminant separator 20. Macro-contaminant outlet 24 is usually smaller in diameter compared to air inlet 23 so that the separated contaminants are not re-entrained into the airflow. Surrounding macro-contaminant outlet 24 and sealed against outer surface 21 is a contaminant chamber 30 having an inner surface 31 for collecting macro-contaminants separated from the airflow by macro-contaminant separator 20. An air outlet 25 is located at the top of macro-contaminant separator 20. Generally, air outlet 25 will be located along the longitudinal axis of macro-contaminant separator 20. Air outlet 25 is connected to a fan chamber 40.

Figure 2:
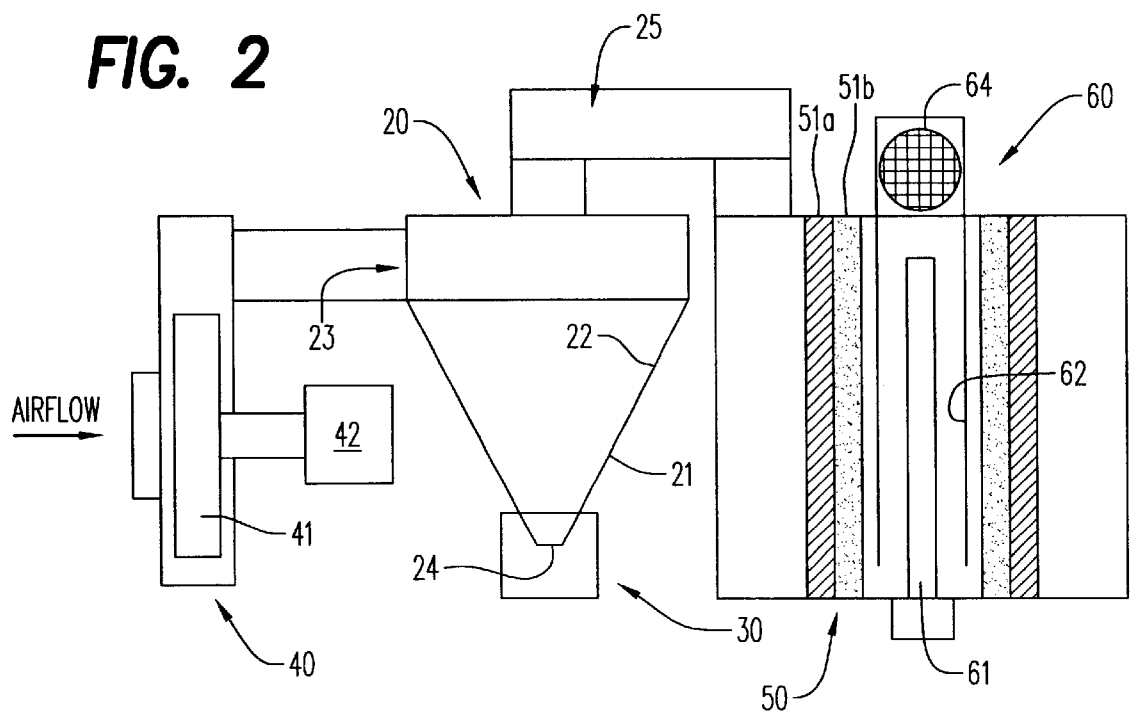
FIG. 2 is a diagram of a second embodiment of a system of cleaning air according to the present invention, in which the blower is located before the macro-contaminant separator.
Figure 3:
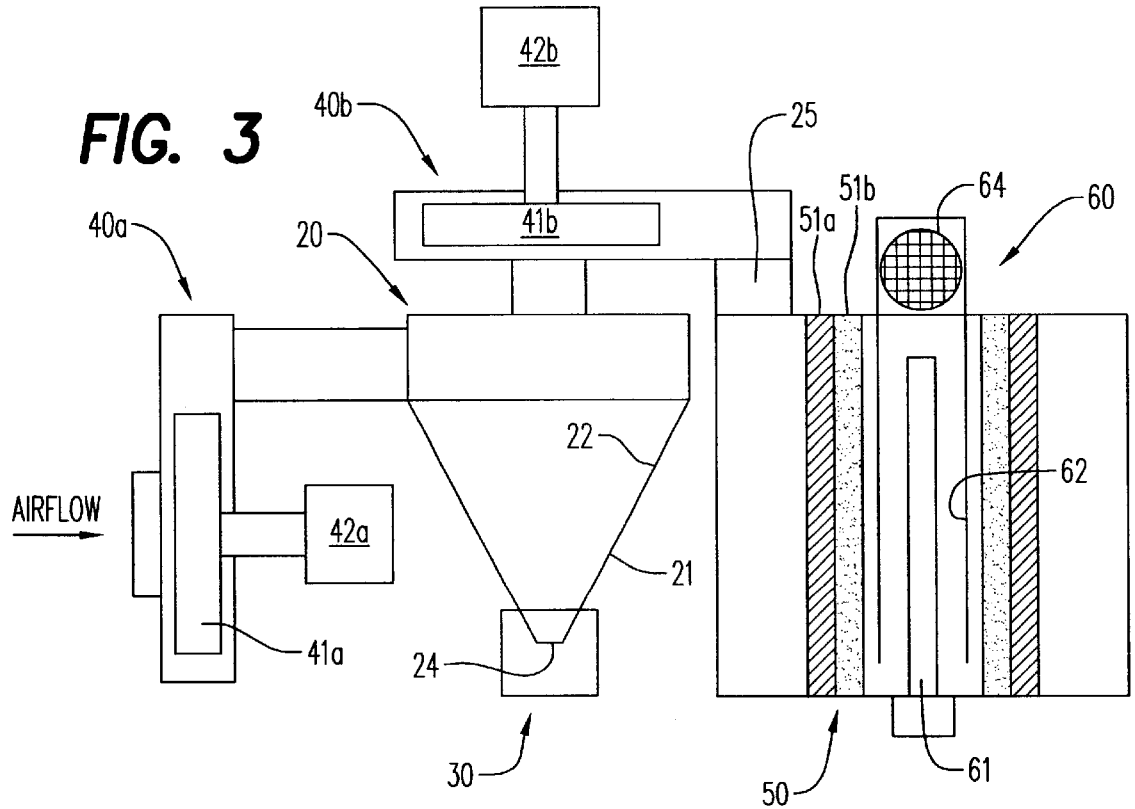
FIG. 3 is a diagram of a third embodiment of a system of cleaning air according to the present invention, in which the system is shown with an independent blower both before and following the macro-contaminant separator.
Figure 4:
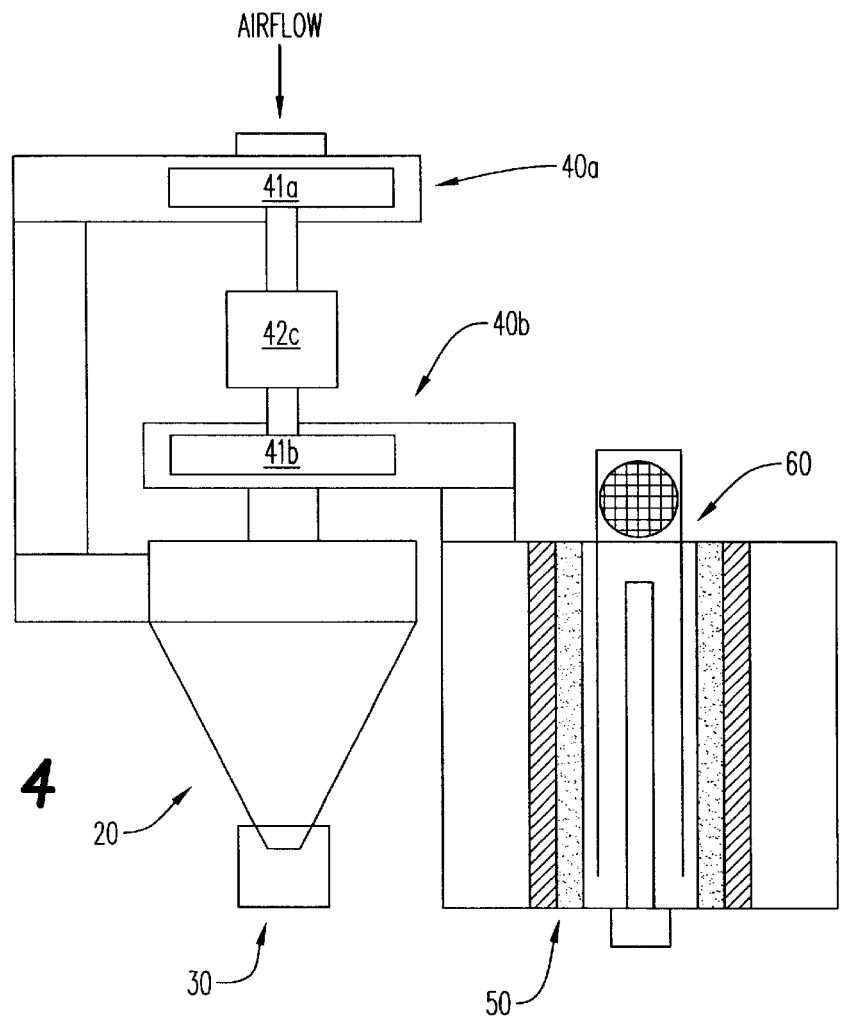
FIG. 4 is a diagram of a fourth embodiment of a system of cleaning air according to the present invention, in which the blowers are driven by a single motor.
Figure 5:
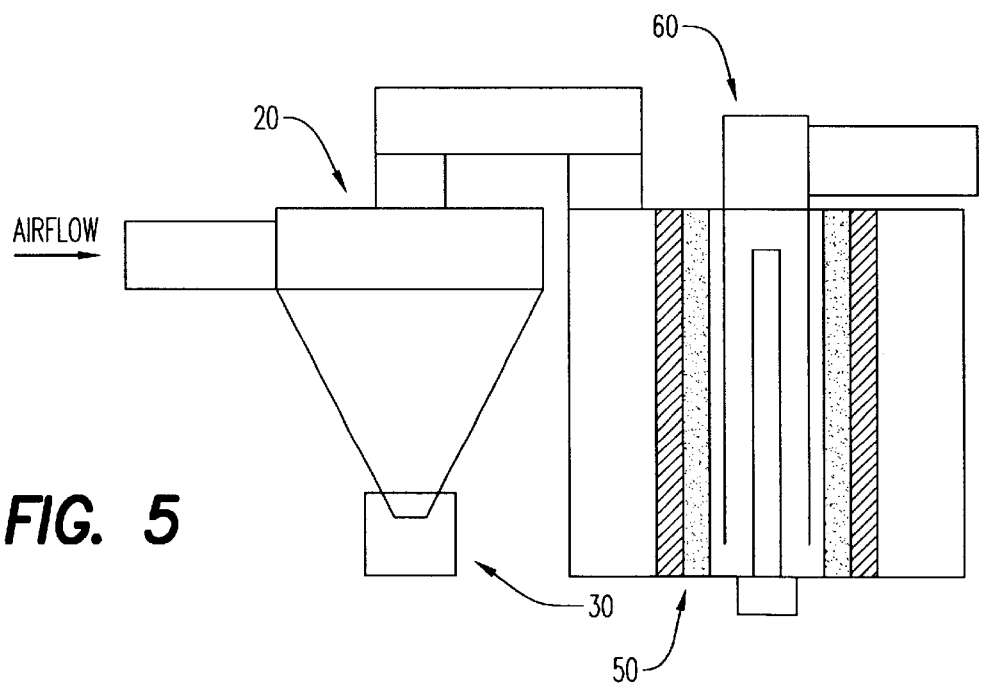
FIG. 5 is a diagram of a fifth embodiment of a system of cleaning air according to the present invention, in which pressure within the system is generated by a separate mechanism (e.g., a forced air heater).

Fan chamber 40 houses a fan 41 that is powered by electric motor 42. Optionally, as illustrated in FIG. 2, fan 41 may be located before macro-contaminant separator 20. Referring to FIG. 3, further opinions include employing at least two fans 41a, 41b that may be driven by one or more fan motors 42a, 42b. FIG. 4 illustrates fans 41a, 41b being driven by a single fan motor 42c. Accordingly, fans may be placed within system 1 as needed. In fact, depending upon the installation requirements, system 1 need not employ fan 41. For example, separate from system 1, a forced air heating, ventilation, and/or cooling system can develop sufficient pressure to drive air into and through system 1. Such a fan-less system is illustrated in FIG. 5.

Referring again to FIG. 1, fan chamber 40 is connected to a micro-contaminant separator 50. Micro-contaminant separator 50 is composed of micro-particle filter 51a, odor adsorber 51b, or a combination thereof. These two filters can remove micro-particles and chemicals from the substantially macro-contaminant free airflow delivered from fan chamber 40.

Micro-particle filter 51 a may be composed of various filter media, such as high-efficiency particulate air (HEPA)

filters, ultra-low particulate air (ULPA) filters, and filters that meet the specifications of the American Society of Heating, Refrigeration, and Air-Conditioning Engineers (ASHRAE).

At a minimum, the filter medium is preferably of a type that is considered a HEPA filter. A HEPA filter, as defined by the Federal Occupational Safety and Health Agency, is a filter that is at least 99.97% efficient in removing monodisperse particles of 0.3 micrometers in diameter. HEPA filters are least effective at removing particles about 0.3 micrometers in diameter. However, both below and above this particle size, the HEPA achieves higher efficiencies. HEPA filter media consist of ultrafine fibers that may be woven or microglass materials, such as glass fibers impregnated with resin. HEPA filters may also be nonwoven materials, such as paper, needle-punched felt of polyester fibers, or a polypropylene trilaminate that includes a meltblown layer and a spunbond layer.

The present invention preferably uses micro-particle filter 51a co-pleated to odor adsorber 51b. Odor adsorber 51b may becomposed of various media know to the art. Preferably, odor adsorber 51b includes activated carbon or zeolite.

Adsorption is the phenomenon whereby molecules adhere to a surface with which they come into contact, due to forces of attraction at the surface. The use of surface energy to attract and hold molecules is physical adsorption. Adsorption is said to occur in three basic steps. These are film diffusion, pore diffusion, and adhesion.

Activated carbon is an extremely efficient adsorptive material because it has an extremely large surface area per unit weight. Trace organic compounds adsorbed by activated carbon include aromatic solvents, polynuclear aromatics, phenolics, chlorinated solvents, and fuels.

Zeolite is a crystalline, porous aluminosilicate. However, some relatively recent discoveries of materials virtually identical to classical zeolite, but consisting of oxide structures with elements other than silicon and aluminum, have stretched the definition. Virtually all types of porous oxide structures are now considered zeolites if they have well-defined pore structures due to a high degree of crystallinity. The zeolitic channels (or pores) are microscopically small, and in fact, have molecular size dimensions such that they are often termed "molecular sieves". The size and shape of the channels have extraordinary effects on the properties of these materials for adsorption processes.

Micro-contaminant separator 50 is connected to a germ controlling chamber 60. Germ controlling chamber 60 contains a germ controlling device. The germ controlling device can be any known to the art. Examples include: chemical germicides, ultraviolet light, laser light, gamma radiation, visible light, high voltage, corona discharge, electron particles, beta particles, ion particles, heat, and cold. Preferably, the germ controlling device is an ultraviolet light source 61. Most preferably, ultraviolet light source 61 is a low-pressure mercury lamp emitting ultraviolet light of about 254 nanometers. The ultraviolet light (1) destroys microorganisms, i.e. bacteria, viruses, pollens, and molds, (2) decomposes residual organic chemicals, and (3) creates negatives ions. Negative ions are considered beneficial for air refreshing.

The micro-particle filter 51a of micro-contaminant separator 50 is substantially shielded from ultraviolet light source 61 by a partition 62, thereby, a radiation zone 65 is created. Preferably, partition 62 is made of a reflective material such as polished aluminum or stainless steel. Partition 62 protects micro-particle filter 51 from photodecomposition caused by ultraviolet light emitted from ultraviolet light source 61. Partition 62 also forces the substantially contaminant free airflow from micro-contaminant separator 50 to travel the entire length of radiation zone 65. Thus, the substantially contaminant free airflow is exposed to the maximum possible amount of radiation.

Exit port 64 vents the contaminant free airflow into the environment from within germ controlling chamber 60. Since exposure to ultraviolet radiation is harmful to living tissue, an ultraviolet light impermeable shield 63 is mounted over exit port 64. Ultraviolet light impermeable shield 63 does not substantially impede the flow of air through exit port 64, but it does prevent ultraviolet light from escaping germ controlling chamber 60.

In use, an airflow, driven by a vacuum created by fan 41 and containing various contaminants, enters macro-contaminant separator 20 via air inlet 23. Because of the tangential entry arrangement and the frustoconical shape of macro-contaminant separator 20, the contaminated airflow takes up a cyclone motion inside macro-contaminant separator 20 and spirals at ever-increasing angular speeds towards macro-contaminant outlet 24.

Macro-contaminants entrained within the contaminated airflow are forced against interior surface 22 of macro-contaminant separator 20 and are subsequently deposited in macro-contaminant collector 30 by gravity and the downward spiraling of the contaminated airflow. The airflow, which is now substantially free of macro-contaminants, such as dirt and dust particles, moves inwardly towards the longitudinal axis of macro-contaminant separator 20 and is taken overhead by fan 41 towards air outlet 25.

Fan 41 pumps the macro-contaminant free airflow removed from macro-contaminant separator 20 via air outlet 25 into micro-contaminant separator 50. The pressurized air permeates through micro-particle filter 51a, odor adsorber 51b, or a combination thereof. Thereby, micro-contaminants are removed from the airflow resulting in a substantially contaminant-free airflow.

The substantially contaminant free airflow then enters radiation zone 65 of germ controlling chamber 60. The airflow is irradiated by ultraviolet source 61 in order to kill or control germs within the substantially contaminant free airflow. By reflecting energy, partition 62 concentrates the ultraviolet light within germ controlling chamber, shields micro-contaminant separator 50, and increases the radiation exposure time of the substantially contaminant-free airflow.

The contaminant-free airflow exits air purifier 1 via air outlet 64, which is covered by ultraviolet light impermeable grid 63.

The invention having been thus described with particular reference to the preferred form thereof, it will be obvious that various changes and modifications may be made therein without departing from the spirit and scope of the invention as defined in the appended claims.

I claim:

1. A system for cleaning an airflow containing macro-contaminants and micro-contaminants, said system comprising:

a cyclone separator that removes said macro-contaminants from said airflow, whereby a substantially macro-contaminant free airflow is created;

a filter that removes said micro-contaminants from said substantially macro-contaminant free airflow and provides a substantially contaminant free airflow; and a germ controller for destroying microorganisms in said substantially contaminant free airflow.

2. The system of claim 1, wherein said filter comprises a micro-particle filter that filters about 75% to about 100% of all contaminants having a particle diameter of about 0.3 micrometers.

3. The system of claim 2, wherein said micro-particle filter means filters about 99.97% of all contaminants having a particle diameter of about 0.3 micrometers.

4. The system of claim 1, wherein said filter comprises an odor adsorber.

5. The system of claim 1, wherein said filter comprises a micro-particle filter and an odor adsorber.

6. The system of claim 5, Wherein said macro-contaminant airflow passes through said micro-particle filter before passing through said odor adsorber.

7. The system of claim 1, wherein said germ controller is at least one selected from the group consisting of: chemical germicides, ultraviolet radiation, electromagnetic radiation, electricity, electrostatic energy, heat, and cold.

8. The system of claim 1, wherein said germ controller is ultraviolet radiation.

9. The system of claim 8, wherein said filter is shielded from said ultraviolet radiation by a partition.

10. The system of claim 1, wherein said airflow is transported throughout said system by a vacuum producer.

11. A process for using a system for removing contaminants from an airflow comprising the steps of:
    separating macro-contaminants from said airflow by causing said airflow to move in a cyclone motion, wherein said macro-contaminants are removed from said airflow by centrifugal force, whereby a substantially macro-contaminant free airflow is created;
    substantially removing micro-contaminants from said substantially macro-contaminant free airflow, whereby a substantially contaminant-free airflow is created; and
    destroying microorganisms in said substantially contaminant free air flow.

12. The process of claim 11, wherein said cyclone motion is created by a means for tangential entry of said airflow into a cyclone particle separator.

13. The process of claim 11, wherein said separating macro-contaminants removes about 50% to about 100% of all contaminant having a particle diameter larger than about 0.3 micrometers from said airflow.

14. The process of claim 11, wherein said step of substantially removing micro-contaminants from said macro-contaminant free airflow, removes about 99.97% of all contaminants having a particle diameter of about 0.3 micrometers from said airflow.

15. The process of claim 11, wherein said step of substantially removing micro-contaminants from said macro-contaminant free airflow includes an odor adsorbing means.

16. The process of claim 11, further comprising the step of substantially controlling or killing germs in said substantially contaminant-free airflow, whereby a contaminant free airflow is created.

17. The process of claim 16, wherein said step of substantially controlling or killing germs in said substantially contaminant-free airflow includes irradiating said contaminant-free airflow with ultraviolet radiation.

18. The system of claim 1, further comprising a fan disposed in a path of said airflow between said separator and said filter, for driving said substantially macro-contaminant free airflow from said separator to said filter.

19. A system for cleaning an airflow, said system comprising:
    a cyclone separator for removing macro-contaminants from said airflow;
    a filter, disposed downstream of said separator, for removing micro-particles from said airflow;
    an adsorber, disposed downstream of said filter, for adsorbing organic compounds from said airflow; and
    a germ controller, disposed downstream of said adsorber, for destroying microorganisms in said airflow.

20. A system for cleaning an airflow, said system comprising:
    a cyclone separator for removing macro-contaminants from said airflow; and
    a device, disposed downstream of said cyclone separator, for performing a function selected from the group consisting of (a) destroying microorganisms in said airflow, and (b) removing residual chemicals from said airflow.

21. A system for cleaning an airflow, said system comprising:
    a cyclone separator for removing macro-contaminants from said airflow; and
    an adsorber, disposed downstream of said cyclone separator, for adsorbing organic compounds from said airflow.

22. The system of claim 21, further comprising a device, disposed downstream of said adsorber, for performing a function selected from the group consisting of (a) destroying microorganisms in said airflow, and (b) removing residual chemicals from said airflow.

23. A system for cleaning an airflow, said system comprising:
    a cyclone separator for removing macro-contaminants from said airflow;
    a filter, disposed downstream of said cyclone separator, for removing micro-particles from said airflow; and
    a device, disposed downstream of said filter, for performing a function selected from the group consisting of (a) destroying microorganisms in said airflow, and (b) removing residual chemicals from said airflow.

* * * * *